(12) United States Patent
Tsukamoto et al.

(10) Patent No.: US 7,034,928 B2
(45) Date of Patent: Apr. 25, 2006

(54) READING APPARATUS

(75) Inventors: Yoshio Tsukamoto, Kanagawa (JP); Akira Kurachi, Tokyo (JP)

(73) Assignee: Baldwin-Japan LTD, (JP)

( * ) Notice: Subject to any disclaimer, the term of this patent is extended or adjusted under 35 U.S.C. 154(b) by 231 days.

(21) Appl. No.: 10/703,784

(22) Filed: Nov. 6, 2003

(65) Prior Publication Data

US 2004/0145727 A1    Jul. 29, 2004

(30) Foreign Application Priority Data

Nov. 7, 2002   (JP)   .............................. 2002-324122

(51) Int. Cl.
  *G06K 9/74* (2006.01)
  *G01N 21/86* (2006.01)
  *G03F 3/08* (2006.01)

(52) U.S. Cl. ................ 356/71; 356/237.2; 250/559.02; 358/518; 358/514

(58) Field of Classification Search ............ 356/71–73, 356/600–601, 607–608, 614, 618–620, 639–640, 356/237.2; 250/559.4, 559.02, 559.42; 358/518, 358/504–505, 512–514, 157, 160
See application file for complete search history.

(56) References Cited

U.S. PATENT DOCUMENTS

| 4,270,047 | A | * | 5/1981 | Mochizuki et al. ......... 250/216 |
| 4,488,808 | A |   | 12/1984 | Kato |
| 4,926,251 | A | * | 5/1990 | Sekizawa et al. ........... 358/535 |
| 5,075,770 | A | * | 12/1991 | Smyth ........................ 358/516 |
| 5,220,626 | A | * | 6/1993 | Suganuma et al. ......... 358/483 |
| 5,305,392 | A |   | 4/1994 | Longest, Jr. et al. |
| 5,321,529 | A | * | 6/1994 | Funada ....................... 358/500 |
| 5,381,167 | A | * | 1/1995 | Fujii et al. .................. 347/116 |
| 5,483,359 | A | * | 1/1996 | Yumiba et al. ............. 358/513 |
| 5,907,414 | A | * | 5/1999 | Hiratsuka ................... 358/513 |
| 6,198,551 | B1 | * | 3/2001 | Tabata ........................ 358/514 |
| 6,512,238 | B1 | * | 1/2003 | Iwaki ....................... 250/559.4 |
| 6,865,000 | B1 | * | 3/2005 | Yushiya ...................... 358/518 |
| 6,924,840 | B1 | * | 8/2005 | Furuhata .................... 348/264 |

OTHER PUBLICATIONS

European Search Report

* cited by examiner

*Primary Examiner*—Gregory J. Toatley, Jr.
*Assistant Examiner*—Sang Hoang Nguyen
(74) *Attorney, Agent, or Firm*—Morgan & Finnegan LLP

(57) ABSTRACT

A reading apparatus comprises a plurality of sensor modules having different resolutions. The sensor modules are arranged in a main scanning direction on a read surface to be used for different purposes of inspecting or identifying.

5 Claims, 4 Drawing Sheets

READING APPARATUS

FIELD OF THE INVENTION

The invention relates to a reading apparatus which can accomplish different purposes of inspecting or identifying alone. For example, the reading apparatus can be used to read a printed surface of newspaper printed by a printing press for inspection of stains, identification of marks or characters and inspection of positional discrepancy between register marks of colors.

PRIOR ART

Regarding a printed surface of newspaper printed by a printing press, three reading apparatuses have heretofore been installed in the printing press. One of the apparatuses comprises a light source and a sensor device to read the printed surface for inspection of stain. Another apparatus also comprises a light source and a sensor device to read the printed surface for identification of mark or character. The other apparatus also comprises a light source and a sensor device to read the printed surface for inspection of positional discrepancy between the register marks of colors.

In this connection, maintenance and cleaning work have therefore been required with respect to the light sources and sensor devices of three reading apparatuses, taking labor and time. In addition, the light sources and sensor devices must be installed at restricted positions and in restricted spaces by reason of the printing press becoming compact. This makes the maintenance and cleaning work difficult. Furthermore, it is expensive to make three reading apparatuses installed.

It is therefore an object of the invention to provide a new and improved reading apparatus, to overcome the above problems.

Other object of the invention is to provide the apparatus which can accomplish different purposes of inspecting or identifying alone.

SUMMARY OF THE INVENTION

According to the invention, a reading apparatus comprises a plurality of sensor modules having different resolutions. The sensor modules are arranged in a main scanning direction on a read surface to be used for different purposes of inspecting or identifying.

In a preferred embodiment, each of the sensor modules includes a linear sensor element, a condenser lens, a sensor drive part, a shading part and a memory part.

The sensor modules comprise first modules each of which has a low resolution, second modules each of which has a middle resolution and third modules each of which has a high resolution. The first, second and third modules are received in a common case to be placed in a row.

The first, second and third modules are used for inspection of stains. The second modules are used for identification of marks or characters. The third modules are used for inspection of positional discrepancy between register marks of colors.

The first modules read the surface to generate image signals of low resolution. The second and third modules read the surface to generate image signals of middle and high resolutions which are then smoothed and divided into those of low resolution when inspecting the stain.

In short, the purposes are for inspection of stain, identification of mark or character and inspection of positional discrepancy between register marks of colors.

The sensor modules are controlled independently from each other. The sensor modules are disposed at positions and in reading ranges for the different purposes of inspecting or identifying in accordance with the different resolutions of sensor modules.

The surface comprises a printed surface.

The apparatus further comprises module control means for making the sensor modules synchronous with a plate cylinder rotated in a printing press to read the surface and generate image signals. The apparatus further comprises a memory in which the image signals are stored. The apparatus further comprises an interface part into which the image signals are taken partially or entirely from the memory, the apparatus image processing the image signals in accordance with the different purposes of inspecting or identifying and then transferring them to systems for inspecting or identifying the quality and kind of read surface.

DETAILED DESCRIPTION OF THE PREFERRED EMBODIMENTS

Figure 1:
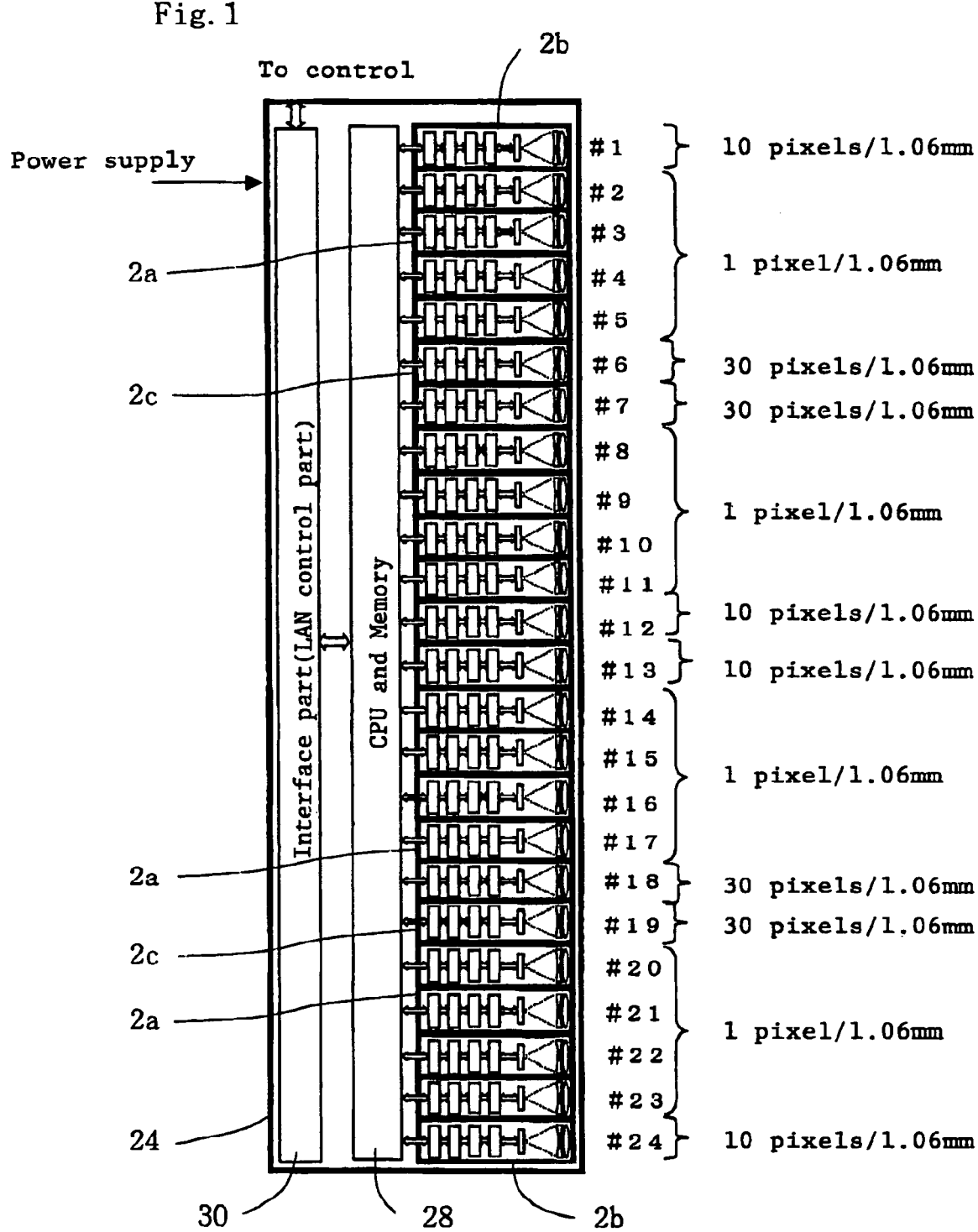
FIG. 1 is an explanatory view of a preferred embodiment of the invention.
Figure 2:
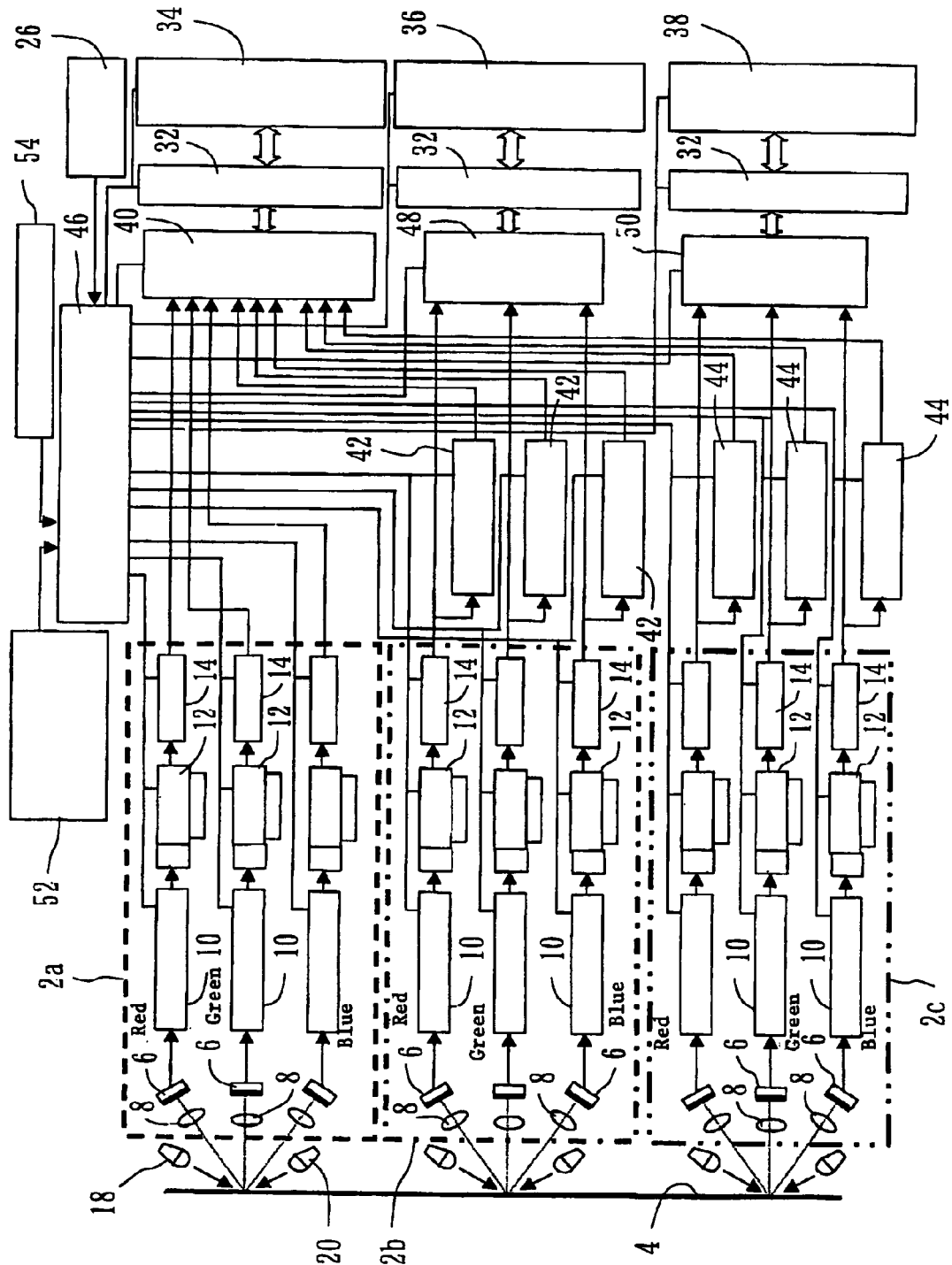
FIG. 2 is a block diagram of the reading apparatus of FIG. 1.

Turning now to the drawings, FIG. 1 illustrates a reading apparatus comprising a plurality of sensor modules 2a, 2b and 2c having different resolutions, according to the invention. The sensor modules 2a, 2b and 2c are arranged in a main scanning direction on a read surface 4, as shown in FIG. 2, to be used for different purposes of inspecting or identifying.

Figure 3:
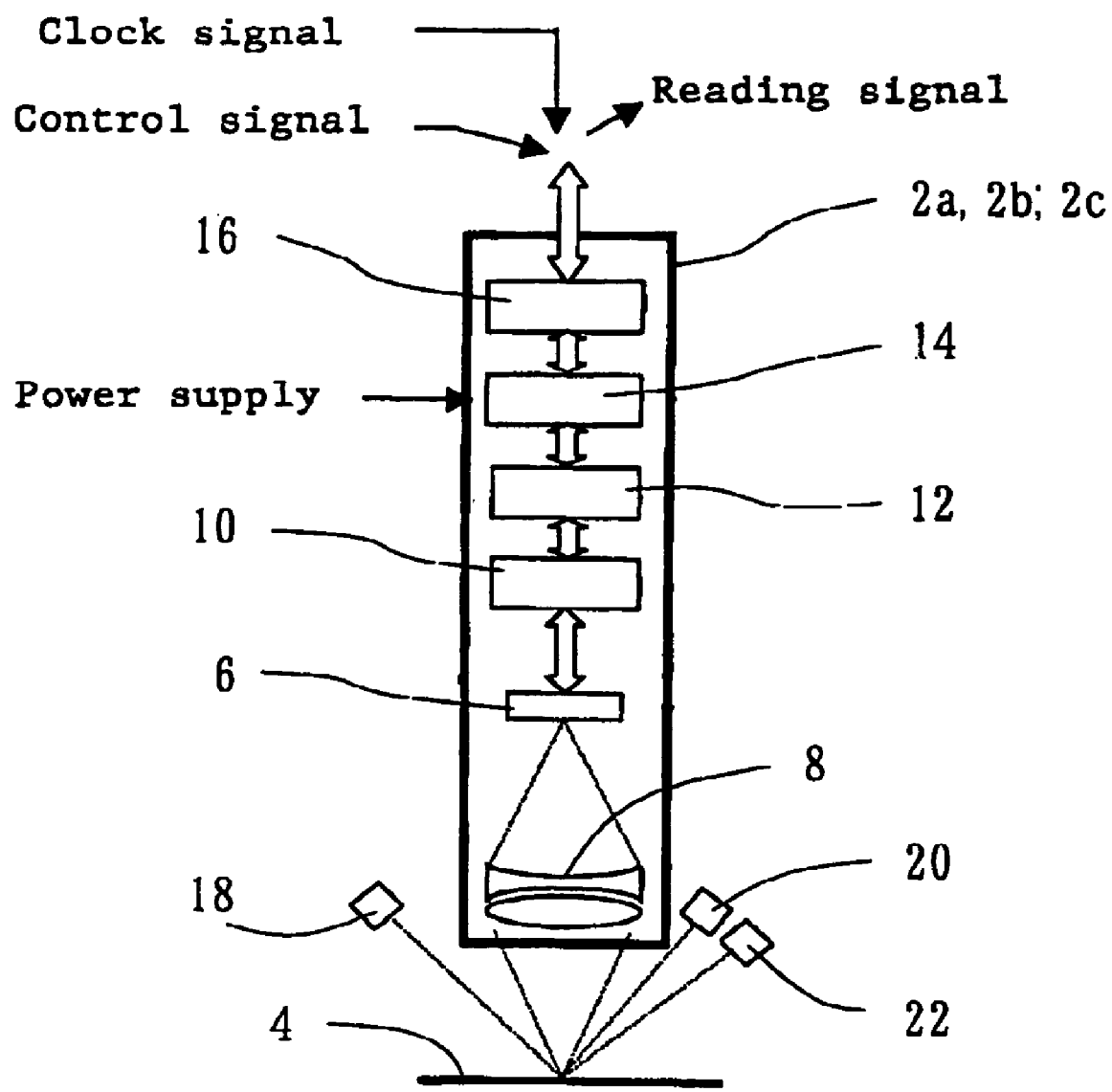
FIG. 3 is an enlarged view of the sensor module of FIG. 1.

Each of the sensor modules 2a, 2b and 2c includes a linear sensor element 6, a condenser lens (micro-lens) 8, a linear sensor drive part (LSI element) 10, an A-D converting and shading part (LSI element) 12, a memory part (memory element) 14 and a communication and interface part (LSI element) 16, as shown in FIG. 3. The surface 4 is illuminated by a red light source 18, a blue light source 20 and a green light source 22 so that light can be reflected from the surface 4. The linear sensor element 6 receives the reflected light passing through the condenser lens 8. The surface 4 comprises a printed surface of newspaper printed by a printing press. The light sources 18, 20 and 22 comprise red, blue and green LEDs. The surface 4 may be illuminated by other light source comprising white LEDs. In this connection, it is preferable that the linear sensor element 6 comprises a linear sensor element for colors (red, blue and green). The linear sensor element for colors 6 receives the reflected light of white and the white light is separated to red, blue and green signals by the linear sensor element for colors. The apparatus then treats image signals of red, blue and green, as shown in FIG. 2.

In the embodiment, the sensor modules include first modules 2a (#2 to #5, #8 to #11, #14 to #17, #20 to #23) each of which has a low resolution. The sensor modules further include second modules 2b (#1, #12, #13 and #24) each of which has a middle resolution. The sensor modules further include third modules 2c (#6, #7, #18 and #19) each of which has a high resolution. The first, second and third modules 2a, 2b and 2c are received in a common case 24 to be placed in a row.

The first, second and third modules 2a, 2b and 2c are used for inspection of stain. The second modules 2b are used for identification of marks or characters. The third modules 2c are used for inspection of positional discrepancy between register marks of colors. In this connection, it should be recognized that a low resolution of 1 pixel/1.06 mm is merely required for inspection of stains. A middle resolution of 10 pixels/1.06 mm is required for identification of marks or characters. A high resolution of 20 to 40 pixels/1.06 mm is required for inspection of positional discrepancy between register marks of colors. Accordingly, each of the first modules 2a merely needs to have the low resolution of 1 pixel/1.06 mm. Each of the second modules 2b needs to have the middle resolution of 10 pixels/1.06 mm. Each of the third modules 2c needs to have the higher solution of 20 to 40 pixels/ 1.06 mm.

By the way, the linear sensor element 6 is a reading sensor element having a length of 5 to 20 mm and comprising, for example, 64, 640 or 1920 semiconductor elements arranged in series. The linear sensor drive LSI element 10 makes the linear sensor element 6 read the surface to generate an image signal which comprises an analogue signal. The image signal is converted into a digital signal by the A-D converting and shading LSI element 12. In addition, the A-D converting and shading LSI element 12 accomplishes a shading compensation against the irregularity of light sources and the irregularity of loss of reflected light passing through the condenser lens 8 to obtain pixels of a uniform value. The image signal is then temporarily stored in the memory element 14 after being converted into the digital signal.

Accordingly, if the pixel has a size of 1 to 10 pixel/1.06 mm and the number of pixels is predetermined into, for example, 64 to 640 pixels per linear sensor element, all the first and second modules 2a and 2b can be set to have a reading width of 68 mm by changing the reducing rate of the condenser lens 8. In this case, one module 2a or 2b can be installed in a cubic content having the width of 68 mm and a height of 180 mm, including the linear sensor element 6, the condenser lens 8, the sensor drive LSI element 10, the A-D converting and shading LSI element 12, the memory element 14 and the communication and interface LSI element 16. In the embodiment, the apparatus includes 16 modules 2a having the low resolution of 1 pixel/1.06 mm and 4 modules 2b having the middle resolution of 10 pixels/1.06 mm.

In addition, if the pixel has a size of 20 to 40 pixels/1.06 mm and the number of pixels is predetermined into, for example, 1280 to 2560 pixels per linear sensor element, all the third modules 2c can be set to have a reading width 68 mm by changing the reducing rate of the condenser lens 8. In this case, on module 2c can be installed in a cubic content having the width of 68 mm and a height of 200 mm, including the same structure as the first and second modules 2a and 2b. In the embodiment, the apparatus includes 4 modules 2c having the high resolution of 30 pixels/1.06 mm. The apparatus has therefore a maximum reading width of 1632 mm when including 24 modules 2a, 2b and 2c arranged.

The apparatus further includes module control means comprising a rotary encoder 26 which detects the rotating speed of a plate cylinder for making the sensor modules 2a, 2b and 2c synchronous with the plate cylinder rotated in the printing press to read the printed surface 4 and generate image signals, as shown in FIG. 2. The sensor modules 2a, 2b and 2c read the printed surface 4 simultaneously with each other at a timing speed which is several times as high as the maximum printing speed of printing press.

The apparatus further includes a CPU and memory 28 in which the image signals are stored. The CPU and memory 28 executes an internal image processing program for image processing the image signals fed from the sensor modules 2a, 2b and 2c in accordance with the purposes of inspecting or identifying. The apparatus further includes a communication and interface part (LAN control part) 30 into which the image signals are taken partially or entirely from the CPU and memory 28. The communication and interface part 30 has three communication and interface circuits 32 for transferring the image signals to a system 34 for inspection of stains, a system 36 for identification of mark or character and a system 38 for inspection of positional discrepancy between register marks of colors, as shown in FIG. 2.

The system 34 is arranged to inspect the stains on the printed surface 4 and determine it good or no good. The system 36 is arranged to identify the marks or characters. The system 38 is arranged to inspect the positional discrepancy between register marks of colors and determine it good or no good.

In this connection, the sensor modules 2a, 2b and 2c are controlled independently from each other. The sensor modules 2a, 2b and 2c are disposed at positions and in reading ranges for the different purposes of inspecting or identifying in accordance with the different resolutions of sensor modules 2a, 2b and 2c.

In addition, the CPU and memory 28 includes a memory 40 in which image signals are stored for inspection of stains. The CPU and memory 28 further includes pixel smoothing and dividing means 42 of 10 pixels to 1 pixel and pixel smoothing and dividing means 44 of 30 pixels to 1 pixel. In the meantime, the first modules 2a read the surface 4 to generate image signals of low resolution of 1 pixel/1.06 mm which are stored in the memory 40 when inspecting the stain in response to a timing and clock signal fed from a signal generating circuit 46. The signal generating circuit 46 is arranged to various timing and clock signals. The second modules 2b also read the surface 4 to generate image signals of middle resolution of 10 pixels/1.06 mm which are then smoothed and divided into those of low resolution of 1 pixel/1.06 mm by the pixel smoothing and dividing means 42 and stored in the memory 40 when inspecting the stain in response to the timing and clock signal. The third modules 2c also read the surface 4 to generate image signals of high resolution of 30 pixels/1.06 mm which are then smoothed and divided into those of low resolution of 1 pixel/1.06 mm by the pixel smoothing and dividing means 44 and stored in the memory 40 when inspecting the stain in response to the timing and clock signal.

Furthermore, the CPU and memory 28 includes a memory 48 in which image signals are stored for identification of marks or characters and a memory 50 in which image signals are stored for inspection of positional discrepancy between register marks of colors. The second module 2b read the surface 4 to generate image signals of middle resolution of 10 pixels/1.06 mm which are stored in the memory 48 when identifying the marks or characters in response a timing and clock signal fed from the signal generating circuit 46. The third modules 2c read the surface 4 to generate image signals of high resolution of 30 pixels/1.06 mm which are stored in the memory 50 when inspecting of positional discrepancy between register marks of colors.

At first, a start signal 52 is fed to the signal generating circuit 46 for start of printing and reading and start of identification of marks or characters and inspection of discrepancy between register marks of colors. A start signal 54 is also fed to the signal generating circuit 46 for start of inspection of stains after confirmation of paper being good.

As to the image signals stored in the memory 40, they are then taken partially or entirely from the memory 40, the communication and interface circuit 32 transferring the image signals to the system 34. As to the image signals stored in the memory 48, they are also taken partially or entirely from the memory 48, the communication and interface circuit 32 transferring the image signals to the system 36. As to the image signals stored in the memory 50, they are also taken partially or entirely from the memory 50, the communication and interface circuit 32 transferring the image signals to the system 38.

Figure 4:
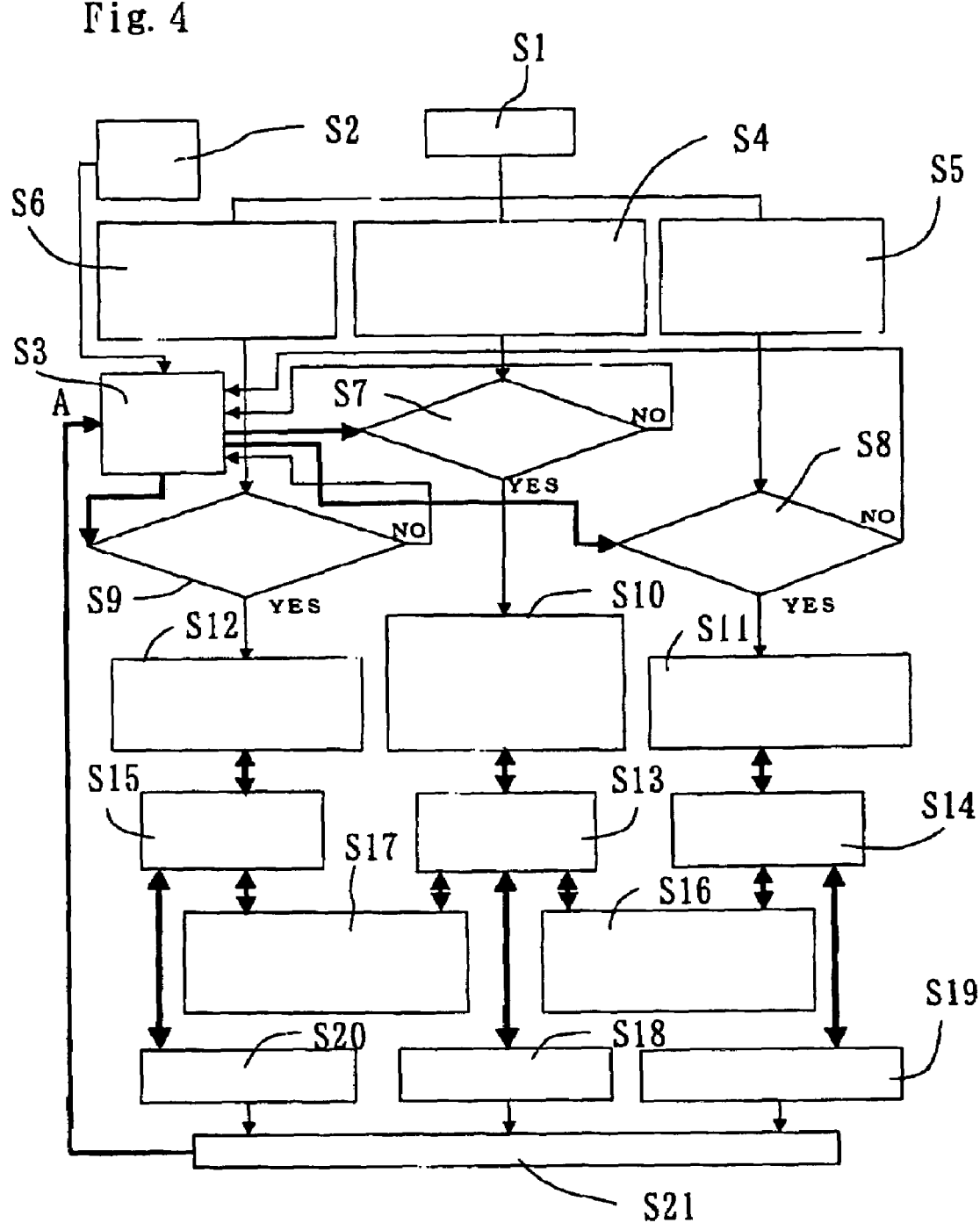
FIG. 4 is a flow chart of reading of the reading apparatus of FIG. 1.

The apparatus should generate a start signal for start of preparation (S1), as shown in FIG. 4. The apparatus should further generate a clock signal for start of reading (S2) which is fed to a clock gate for indication of start of reading (S3). The first modules 2a (#2 to #51 #8 to #11, #14 to #17 and #20 to #23) read the printed surface 4 (S4), the second modules 2b (#1, #12, #13 and #24) reading the printed surface 4 (S5), the third modules 2c (#6, #7, #18 and #19) reading the printed surface (S6). The apparatus determines whether the first modules 2a has the lower resolution of 1 pixel/1.06 mm or not (S7), whether the second modules 2b has the middle resolution of 10 pixels/1.06 mm or not (S8) and whether the third modules 2c has the high resolution of 30 pixels/1.06 mm or not (S9). The image signals are stored in the memories 14 (S10, S11 and S12). The image signals are then stored in the memories 40, 48 and 50 (S13, S14 and S15). As to the image signals of middle resolution of 10 pixels/1.06 mm, they are smoothed and divided into those of low resolution of 1 pixel/1.06 mm and then stored in the memory 40 (S16). As to the image signals of high resolution of 30 pixels/1.06 mm, they are also smoothed and divided into those of low resolution of 1 pixel/1.06 mm (S17). The apparatus transfers the image signals to the system 34 for inspection of stains (S18), the system 36 for identification of marks or characters (S19) and the system 38 for inspection of discrepancy between register marks of colors (S20). A return signal is fed to the clock gate at A after reading and restoring for repetition (S21).

The apparatus can be used for inspection of stains, identification of marks or characters and inspection of positional discrepancy between register marks of colors, as described above. Accordingly, unlike the prior art, it is not required to make three reading apparatuses installed in a printing press. Maintenance and cleaning work can therefore be done without taking labor and time. In comparison with three reading apparatuses, it is very economical to make the apparatus installed.

What is claimed is:

1. A reading apparatus comprising:

a plurality of sensor modules having different resolutions, said sensor modules being arranged in a main scanning direction on a read surface to be used for different purposes of inspecting or identifying, wherein said sensor modules comprise first modules each of which has a low resolution, second modules each of which has a middle resolution and third modules each of which has a high resolution, said first, second and third modules being received in a common case to be placed in a row.

2. The apparatus as set forth in claim 1 wherein said first, second and third modules are used for inspection of stains, said second modules being used for identification of marks or characters, the third modules being used for inspection of positional discrepancy between register marks of colors.

3. The apparatus as set forth in claim 2 wherein said first modules read said read surface to generate image signals of low resolution, the second and third modules reading said read surface to generate image signals of middle and high solutions which are then smoothed and divided into those of low resolution when inspecting the stains.

4. A reading apparatus comprising:

a plurality of sensor modules having different resolutions, said sensor modules being arranged in a main scanning direction on a read surface to be used for different purposes of inspecting or identifying, wherein said purposes are for inspection of stains, identification of marks or characters and inspection of discrepancy between register marks of colors.

5. A reading apparatus comprising:

a plurality of sensor modules having different resolutions, said sensor modules being arranged in a main scanning direction on a read surface to be used for different purposes of inspecting or identifying;

module control means for making said sensor modules synchronous with a plate cylinder rotated in a printing press to read said read surface and generate image signals;

a memory in which the image signals are stored;

an interface part into which said image signals are taken partially or entirely from said memory, said apparatus image processing said image signals in accordance with said different purpose of inspecting or identifying and then transferring said image signals to systems for inspecting or identifying the quality and kind of said read surface.

* * * * *